(12) United States Patent
Nicholas et al.

(10) Patent No.: US 11,389,144 B2
(45) Date of Patent: *Jul. 19, 2022

(54) HAND-HELD SURGICAL DEVICES

(71) Applicant: Covidien LP, Mansfield, MA (US)

(72) Inventors: David A. Nicholas, Trumbull, CT (US);
David A. Zeichner, Oxford, CT (US);
David Malinouskas, Monroe, CT (US)

(73) Assignee: Covidien LP, Mansfield, MA (US)

( * ) Notice: Subject to any disclaimer, the term of this patent is extended or adjusted under 35 U.S.C. 154(b) by 151 days.

This patent is subject to a terminal disclaimer.

(21) Appl. No.: 16/860,472

(22) Filed: Apr. 28, 2020

(65) Prior Publication Data

US 2020/0253591 A1    Aug. 13, 2020

Related U.S. Application Data

(63) Continuation of application No. 15/652,418, filed on Jul. 18, 2017, now Pat. No. 10,660,626, which is a
(Continued)

(51) Int. Cl.
*A61B 17/068* (2006.01)
*A61B 17/00* (2006.01)
(Continued)

(52) U.S. Cl.
CPC ...... *A61B 17/00234* (2013.01); *A61B 17/068* (2013.01); *A61B 17/07207* (2013.01);
(Continued)

(58) Field of Classification Search
CPC ............ A61B 17/00234; A61B 17/068; A61B 17/7207; A61B 34/70
See application file for complete search history.

(56) References Cited

U.S. PATENT DOCUMENTS

| 2,777,340 A | 1/1957 | Hettwer et al. |
| 2,957,353 A | 10/1960 | Babacz |
| (Continued) | | |

FOREIGN PATENT DOCUMENTS

| AU | 2008229795 A1 | 4/2009 |
| AU | 2011201182 B2 | 4/2014 |
| (Continued) | | |

OTHER PUBLICATIONS

Japanese Notice of Reasons for Rejection (with English Translation), dated Apr. 21, 2015, corresponding to Japanese Patent Application No. 2011-090475; 4total pages.

(Continued)

*Primary Examiner* — Nathaniel C Chukwurah (57) ABSTRACT

A surgical system includes an intelligent surgical device having a drive motor supported in the housing and being in electrical communication with the power source; and control circuitry. The control circuitry includes a feedback system for monitoring a condition of the surgical device during a use thereof and for changing an operative parameter of the surgical device when a change in the monitored condition occurs. The surgical system includes a non-intelligent loading unit for selective connection to the housing of the surgical device and which is actuatable by the drive motor, the loading unit having a first and a second condition. During operation, the drive motor actuates the loading unit from the first condition to the second condition; and when the loading unit achieves the second condition, a change in the at least one monitored condition occurs and an operative parameter of the surgical device is changed.

15 Claims, 6 Drawing Sheets

Related U.S. Application Data continuation of application No. 13/955,237, filed on Jul. 31, 2013, now Pat. No. 9,706,981, which is a continuation of application No. 13/039,677, filed on Mar. 3, 2011, now Pat. No. 8,517,241.

(60) Provisional application No. 61/324,919, filed on Apr. 16, 2010.

(51) Int. Cl.
  *A61B 17/072* (2006.01)
  *A61B 34/00* (2016.01)
  *A61B 90/00* (2016.01)

(52) U.S. Cl.
  CPC .... *A61B 34/70* (2016.02); *A61B 2017/00398* (2013.01); *A61B 2017/00473* (2013.01); *A61B 2090/0814* (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,331,277 A | 5/1982 | Green |
| 4,606,343 A | 8/1986 | Conta et al. |
| 4,705,038 A | 11/1987 | Sjostrom et al. |
| 4,722,685 A | 2/1988 | de Estrada et al. |
| 4,807,628 A | 2/1989 | Peters et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,143,453 A | 9/1992 | Weynant nee Girones |
| 5,152,744 A | 10/1992 | Krause et al. |
| 5,268,622 A * | 12/1993 | Philipp .............. A61B 17/1626 318/400.08 |
| RE34,519 E | 1/1994 | Fox et al. |
| 5,301,061 A | 4/1994 | Nakada et al. |
| 5,312,023 A | 5/1994 | Green et al. |
| 5,313,935 A | 5/1994 | Kortenbach et al. |
| 5,326,013 A | 7/1994 | Green et al. |
| 5,339,799 A | 8/1994 | Kami et al. |
| 5,350,355 A | 9/1994 | Sklar |
| 5,359,993 A | 11/1994 | Slater et al. |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,595 A | 5/1997 | Sklar et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,256 A | 6/1998 | Mastri et al. |
| 5,762,603 A | 6/1998 | Thompson |
| 5,769,791 A | 6/1998 | Benaron et al. |
| 5,779,130 A | 7/1998 | Alesi et al. |
| 5,782,396 A | 7/1998 | Mastri et al. |
| 5,782,397 A | 7/1998 | Koukline |
| 5,817,093 A | 10/1998 | Williamson, IV et al. |
| 5,820,009 A | 10/1998 | Melling et al. |
| 5,823,066 A | 10/1998 | Huitema et al. |
| 5,830,121 A | 11/1998 | Enomoto et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,991,355 A | 11/1999 | Dahlke |
| 5,992,724 A | 11/1999 | Snyder |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,166,538 A | 12/2000 | D'Alfonso |
| 6,236,874 B1 | 5/2001 | Devlin et al. |
| 6,237,604 B1 | 5/2001 | Burnside et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,295,330 B1 | 9/2001 | Skog et al. |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,387,092 B1 | 5/2002 | Burnside et al. |
| 6,388,240 B2 | 5/2002 | Schulz et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,515,273 B2 | 2/2003 | Al-Ali |
| 6,533,157 B1 | 3/2003 | Whitman |
| 6,537,280 B2 | 3/2003 | Dinger et al. |
| 6,578,579 B2 | 6/2003 | Burnside et al. |
| 6,601,748 B1 | 8/2003 | Fung et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,651,669 B1 | 11/2003 | Burnside |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |

(56) References Cited

U.S. PATENT DOCUMENTS

| | | |
|---|---|---|
| 6,861,639 B2 | 3/2005 | Al-Ali |
| 6,891,941 B1 | 5/2005 | Barthel et al. |
| 6,899,538 B2 | 5/2005 | Matoba |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| 7,048,687 B1 | 5/2006 | Reuss et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,118,564 B2 | 10/2006 | Ritchie et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,225,964 B2 | 6/2007 | Mastri et al. |
| 7,238,021 B1 | 7/2007 | Johnson |
| 7,240,817 B2 | 7/2007 | Higuchi |
| 7,241,270 B2 | 7/2007 | Horzewski et al. |
| 7,246,734 B2 | 7/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,721,936 B2 | 5/2010 | Shalton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 * | 8/2013 | Nicholas ............ A61B 17/068 227/175.3 |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |

(56) References Cited

U.S. PATENT DOCUMENTS

| | | |
|---|---|---|
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,706,981 B2 | 7/2017 | Nicholas et al. |
| 10,660,626 B2 * | 5/2020 | Nicholas ............ A61B 17/07207 |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0073981 A1 | 4/2003 | Whitman et al. |
| 2003/0125717 A1 | 7/2003 | Whitman |
| 2003/0165794 A1 | 9/2003 | Matoba |
| 2004/0094597 A1 | 5/2004 | Whitman et al. |
| 2004/0111012 A1 | 6/2004 | Whitman |
| 2004/0111081 A1 | 6/2004 | Whitman et al. |
| 2004/0133189 A1 | 7/2004 | Sakurai |
| 2004/0176751 A1 | 9/2004 | Weitzner et al. |
| 2004/0232199 A1 | 11/2004 | Shelton et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006434 A1 | 1/2005 | Wales et al. |
| 2005/0023324 A1 | 2/2005 | Doll et al. |
| 2005/0131442 A1 | 6/2005 | Yachia et al. |
| 2005/0139636 A1 | 6/2005 | Schwemberger et al. |
| 2005/0187576 A1 | 8/2005 | Whitman et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2006/0022014 A1 | 2/2006 | Shelton et al. |
| 2006/0022015 A1 | 2/2006 | Shelton et al. |
| 2006/0142656 A1 | 6/2006 | Malackowski et al. |
| 2006/0142740 A1 | 6/2006 | Sherman et al. |
| 2006/0151567 A1 | 7/2006 | Roy |
| 2006/0273135 A1 | 12/2006 | Beetel |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0055219 A1 | 3/2007 | Whitman et al. |
| 2007/0055304 A1 | 3/2007 | Whitman |
| 2007/0084896 A1 | 4/2007 | Doll et al. |
| 2007/0084897 A1 | 4/2007 | Shelton et al. |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0125826 A1 | 6/2007 | Shelton |
| 2007/0152014 A1 | 7/2007 | Gillum et al. |
| 2007/0158385 A1 | 7/2007 | Hueil et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |
| 2007/0175964 A1 | 8/2007 | Shelton et al. |
| 2007/0187453 A1 | 8/2007 | Smith et al. |
| 2007/0219563 A1 | 9/2007 | Voegele |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0039831 A1 | 2/2008 | Odom et al. |
| 2008/0048002 A1 | 2/2008 | Smith et al. |
| 2008/0058801 A1 | 3/2008 | Taylor et al. |
| 2008/0078801 A1 | 4/2008 | Shelton et al. |
| 2008/0109012 A1 | 5/2008 | Falco et al. |
| 2008/0110957 A1 | 5/2008 | McBride et al. |
| 2008/0110958 A1 | 5/2008 | McKenna et al. |
| 2008/0135600 A1 | 6/2008 | Hiranuma et al. |
| 2008/0164296 A1 | 7/2008 | Shelton et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0277449 A1 | 11/2008 | Marczyk |
| 2008/0300580 A1 | 12/2008 | Shelton, IV et al. |
| 2008/0308603 A1 | 12/2008 | Shelton et al. |
| 2008/0308607 A1 | 12/2008 | Timm et al. |
| 2009/0090763 A1 | 4/2009 | Zemlok et al. |
| 2009/0099876 A1 | 4/2009 | Whitman |
| 2009/0101692 A1 | 4/2009 | Whitman et al. |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |

(56) References Cited

U.S. PATENT DOCUMENTS

| | | |
|---|---|---|
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| AU | 2014204542 B2 | 5/2016 |
| CA | 2451558 A1 | 1/2003 |
| CN | 1547454 A | 11/2004 |
| CN | 1961839 A | 5/2007 |
| CN | 101224116 A | 7/2008 |
| CN | 101401736 A | 4/2009 |
| CN | 101856251 A | 10/2010 |
| CN | 102188270 A | 9/2011 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0679367 A2 | 11/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943968 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 B1 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08038488 | 2/1996 |
| JP | 2005125075 A | 5/2005 |
| JP | 2009090113 A | 4/2009 |
| JP | 2011189128 A | 9/2011 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007026354 A1 | 3/2007 |
| WO | 2007137304 A2 | 11/2007 |
| WO | 2008103797 A2 | 8/2008 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |
| WO | 2014194317 A1 | 12/2014 |

OTHER PUBLICATIONS

European Search Report corresponding to EP 11250473 dated Aug. 3, 2011; (3 pp).

(56) References Cited

OTHER PUBLICATIONS

Australian Patent Examination Report No. 1, dated Jan. 7, 2016, corresponding to Australian Patent Application No. 2014204542; 4 pages.
Japanese Notice of Reasons for Rejection (with English Translation), dated Nov. 13, 2015, corresponding to Japanese Patent Application No. 2011-090475; 4 total pages.
European Search Report dated Jul. 26, 2016, corresponding to European Application No. 16156453.9; 9 pages.
Japanese Notice of Allowance and English language Summary Form dated Jun. 19, 2016, corresponding to Japanese Application No. 2011-090475; 4 pages.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Canadian Office Action and Examination Report dated Oct. 20, 2016, corresponding to Canadian Applciation No. 2,733,801; 3 pages.
Chinese Office Action (with English Translation), dated Dec. 1, 2016, corresponding to Chinese Application No. 201510310141.8; 20 total pages.
Australian Examination Report 1 dated Nov. 15, 2018, corresponding to Australian Application No. 2018200975; 2 pages.
Extended European Search Report corresponding to EP 11 25 0462.6, completed Jul. 20, 2011 and dated Jul. 28, 2011; (6 pp.).

Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013 (6 pp.).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
European Search Report No. 13189650.8 dated Sep. 10, 2014.
Chinese Office Action from Application No. CN 201310198745.9 dated Oct. 29, 2014.
Canadian Office Action dated May 7, 2015 issued in Canadian Application No. 2,640,399.
Japanese Official Action and English language translation dated Jun. 2, 2015 from Appl. No. JP 2014-148482.
Australian Examination Report from Appl. No. AU 2014210681 dated Aug. 13, 2015.
European Examination Report from Appl. No. EP 14 182 013.4-1654 dated Aug. 14, 2015.
Chinese Office Action and English language translation issued in Appl. No. CN 201410083679.5 dated Feb. 23, 2017.
Australian Examination Report from Appl. No. AU 2016200924 dated Mar. 2, 2017.
Australian Examination Report issued in Appl. No. AU 2014200501 dated May 2, 2017.
Extended European Search Report issued in Appl. No. EP 17157550.9 dated Jun. 22, 2017.
Extended European Search Report issued in Appl. No. EP 17161135.3 dated Jun. 12, 2017.
European Examination Report issued in Appl. No. EP 16151576.2 dated Jun. 23, 2017.
Canadian Office Action dated Sep. 11, 2017 in Appl. No. CA 2,935,353 (4 pages).
European Search Report for corresponding EP11250473 dated Aug. 3, 2011 (3 pages).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).

(56) References Cited

OTHER PUBLICATIONS

Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).

* cited by examiner

HAND-HELD SURGICAL DEVICES

CROSS REFERENCE TO RELATED APPLICATIONS

The present application is a continuation application of U.S. patent application Ser. No. 15/652,418, filed on Jul. 18, 2017, now U.S. Pat. No. 10,660,626, which is a continuation application of U.S. patent application Ser. No. 13/955,237, filed on Jul. 31, 2013, now U.S. Pat. No. 9,706,981, which is a continuation application of U.S. patent application Ser. No. 13/039,677, filed on Mar. 3, 2011, now U.S. Pat. No. 8,517,241, which claims the benefit of and priority to U.S. Provisional Application Ser. No. 61/324,919 filed on Apr. 16, 2010, the entire contents of each of which are incorporated by reference herein.

BACKGROUND

1. Technical Field

The present disclosure relates to surgical devices and/or systems. More specifically, the present disclosure relates to hand-held surgical devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating the surgical device. In many instances the surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In intelligent surgical devices, intelligent disposable loading units and/or single use loading units include an identification element which communicates with a reader element disposed within an intelligent powered handle assembly. In this manner, when the intelligent disposable loading units and/or single use loading units are connected to the intelligent handle assembly, the reader element of the intelligent handle assembly communicates with the identification element of the intelligent disposable loading units and/or single use loading units to thereby indicate to the intelligent handle assembly which particular loading unit is attached thereto. Once the particular loading unit, attached to the handle assembly is identified, operative parameters for the powered handle assembly may be set in accordance with predetermined values.

A need exists for a system that is able to detect particular parameters (e.g., length of a staple cartridge, indication that a staple cartridge has been fired) of non-intelligent (i.e., not including an identification member) disposable loading units and/or single use loading units when such non-intelligent disposable loading units and/or single use loading units are connected to intelligent handle assemblies.

SUMMARY

The present disclosure relates to hand-held surgical devices and/or systems configured for use with removable disposable loading units and/or single use loading units for clamping, cutting and/or stapling tissue.

According to an aspect of the present disclosure, a surgical system for performing a surgical procedure is provided. The surgical system includes an intelligent surgical device having a housing; a power source supported in the housing; at least one drive motor supported in the housing and being in electrical communication with the power source; and control circuitry interfacing with the power source and the at least one drive motor. The control circuitry includes a feedback system for monitoring at least one condition of the surgical device during a use thereof and for changing an operative parameter of the surgical device when a change in the at least one monitored condition occurs. The surgical system includes at least one non-intelligent loading unit configured for selective connection to the housing of the surgical device and which is actuatable by the at least one drive motor, the loading unit having at least a first condition and a second condition. During operation of the surgical device, the at least one drive motor actuates the loading unit from the first condition to at least the second condition; and when the loading unit achieves the second condition, a change in the at least one monitored condition occurs and an operative parameter of the surgical device is changed.

The at least one condition monitored by the feedback system may be a voltage being delivered to the at least one drive motor. The feedback system may include a resistor of a known quantity associated with the voltage being delivered to the at least one drive motor. The feedback system may calculate a current level across the resistor.

The operative parameter of the surgical device may be changed when the feedback system determines a current level across the resistor exceeds a threshold current level.

The second condition of the loading unit may be an end of a firing stroke thereof.

The current level across the resistor may exceed the threshold current level when the end of the firing stroke of the loading unit is reached.

The operative parameter of the surgical device that is changed when the feedback system determines that the current level across the resistor exceeds the threshold current level may be a voltage that is delivered to the at least one drive motor.

The operative parameter of the surgical device that is changed may be a power delivered to the at least one motor.

The second condition of the loading unit may be an end of a firing stroke thereof.

The surgical system may further include a plurality of non-intelligent loading units, wherein each loading unit includes a different unique second condition. The second condition of each loading unit may correspond to a different unique length of a firing stroke of each loading unit. The at least one condition monitored by the feedback system may be a voltage being delivered to the at least one drive motor, wherein the feedback system may include a resistor of a known quantity associated with the voltage being delivered to the at least one drive motor, and wherein the feedback system may calculate a current level across the resistor, and wherein the operative parameter of the surgical device may be changed when the feedback system determines a current level across the resistor exceeds a threshold current level.

The current level across the resistor may exceed the threshold current level when the end of the firing stroke of any of the plurality of loading units is reached. The operative parameter of the surgical device that is changed when the feedback system determines that the current level across the resistor exceeds the threshold current level may be a voltage that is delivered to the at least one drive motor.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed surgical device are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

Referring initially to FIGS. 1-4, a hand-held powered surgical device in accordance with an embodiment of the present disclosure is shown and generally designated 10. Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, now U.S. Pat. No. 10,588,629, the entire content of each of which is incorporated herein by reference, for a detailed description of the construction and operation of exemplary surgical devices 10.

Surgical device 10 includes a housing having lower portion 12 forming a base, and an intermediate portion 14, which includes several finger-actuated control buttons 17 and 18 and rocker device 27. Lower portion 12 is configured to selectively store a power source in the form of a battery or the like (not shown). Intermediate portion 14 is configured and adapted to house at least one drive motor (not shown) that is powered by the power source. Surgical device 10 further includes control circuitry (not shown) therein which controls the operation of surgical device 10 based on input from a user and/or feedback obtained prior to, during or after operation of surgical device 10.

Control buttons 17 and 18 and rocker device 27 are located at a front location of the intermediate portion 14 of surgical device 10. Each one of the control buttons 17, 18, and rocker device 27 includes a respective magnet that is moved by the actuation of a user, or operator. In addition, a circuit board (not shown) disposed within surgical device 10 includes, for each one of the control buttons 17, 18 and rocker device 27, respective Hall-effect switches that are actuated by the movement of the magnets in the control buttons 17, 18 and rocker device 27. The actuation of the Hall-effect switch causes the circuit board to provide appropriate signals to a function selection module and an actuator or input drive component to actuate or operate loading unit 20.

Surgical devices 10 may include at least one drive motor, at least one power source "PS" (see FIG. 5) for powering the at least one drive motor, and at least one rotatable drive shaft connected to the drive motor.

In accordance with the present disclosure, surgical device 10 includes a first and a second drive motor, and a first and a second rotatable drive member or shaft, respectively connected to the first and second drive motors. In use, as the first drive motor is activated, the first drive motor will cause the first drive shaft to selectively rotate along its axis in either a first or clock-wise direction, or in a second or counter clock-wise direction. Additionally, as the second drive motor is activated, the second drive motor will cause the second drive shaft to selectively rotate along its axis in either a first or clock-wise direction, or in a second or counter clock-wise direction.

Surgical device 10 is shown in FIGS. 1-4 interfacing with an adapter assembly 100 configured to interconnect surgical device 10 with disposable loading units (DLUs) and/or single use loading units (SULUs) (hereinafter, "loading units"). Reference may be made to U.S. Provisional Application Ser. No. 61/308,045, filed on Feb. 25, 2010, the entire content of which is incorporated herein by reference, for a detailed description of the construction and operation of exemplary adapter assemblies 100.

As seen in FIGS. 1-4, adapter assembly 100 is configured and adapted to operatively interconnect and couple any one of a number of loading units to surgical device 10. For example, adapter assembly 100 is configured and adapted to operatively interconnect and couple an endo-gastrointestinal anastomosis loading unit 20 including a staple line length of 30 mm, 45 mm or 60 mm.

Reference may be made to U.S. Patent Publication No. 2009/0145947, filed Jan. 14, 2009, the entire content of which is incorporated herein by reference for a detailed discussion of the construction and operation of the endo-gastrointestinal anastomosis loading unit 20.

Loading units 20 include at least one axially translatable drive member therein that is configured and adapted to at least one of open and close jaw assemblies thereof by approximating or separating an anvil assembly and a cartridge assembly to/away from one another, and to fire the loading unit to expel staples contained in the cartridge assembly for formation against the anvil assembly and possibly to actuate a knife blade along the staple line. Loading units 20 may further include an axially translatable drive member therein that is configured and adapted to cause an articulation thereof.

Loading units 20 are non-intelligent in that loading units 20 typically do not include any identification members, in the form of sensors or the like, which interact with reader elements disposed in surgical device 10 for identification thereof and for identification of parameters (e.g., length of a staple cartridge, indication that a staple cartridge has been fired) thereof.

Figure 1:
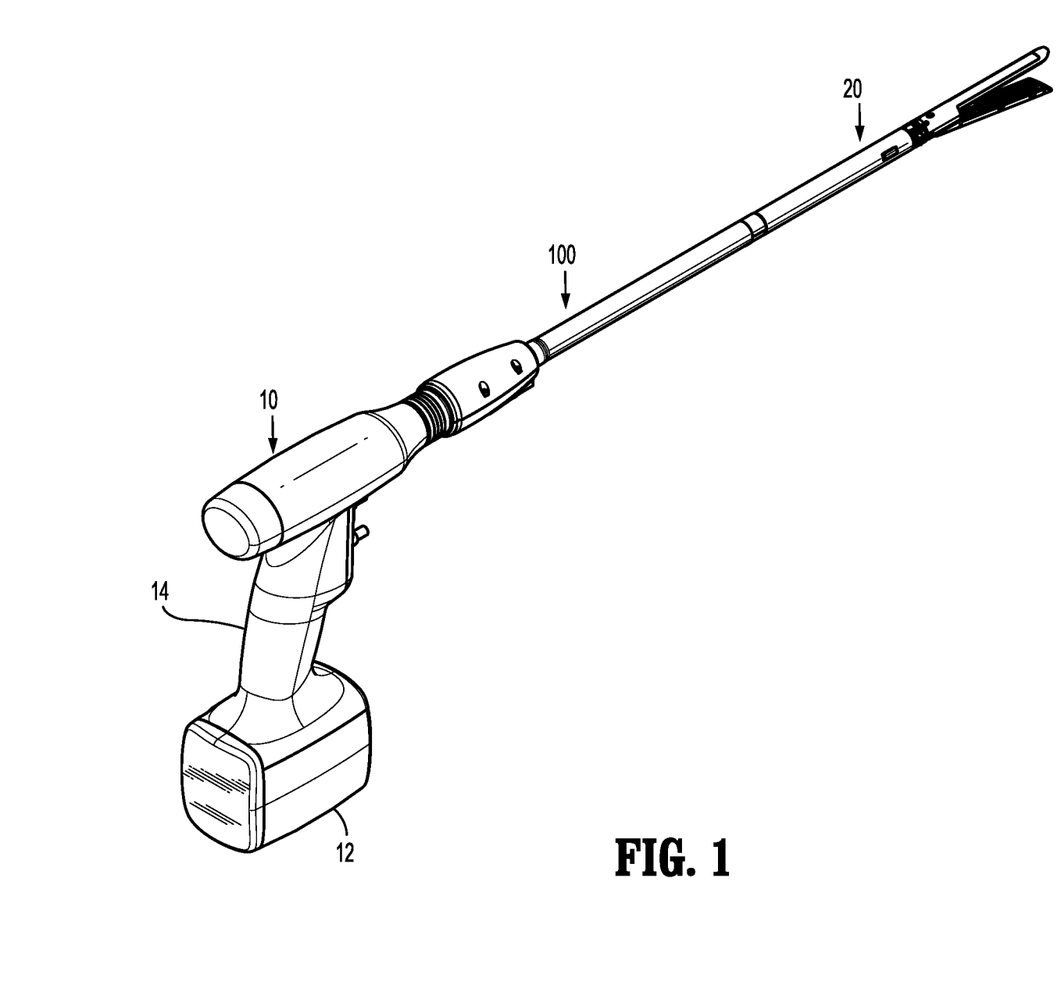
FIG. 1 is a rear, perspective view of an exemplary intelligent surgical device and/or handle assembly supporting an adapter assembly and illustrating an exemplary loading unit supported on an end of the adapter assembly.
Figure 2:
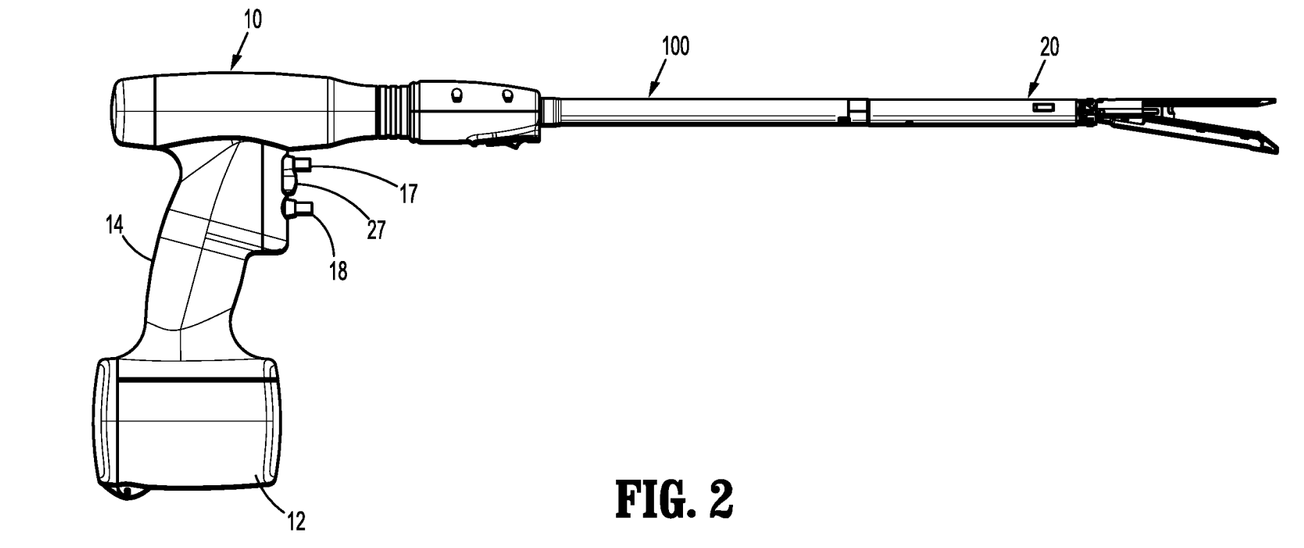
FIG. 2 is a side, elevational view of the intelligent surgical device, adapter assembly and loading unit shown in FIG. 1.
Figure 3:
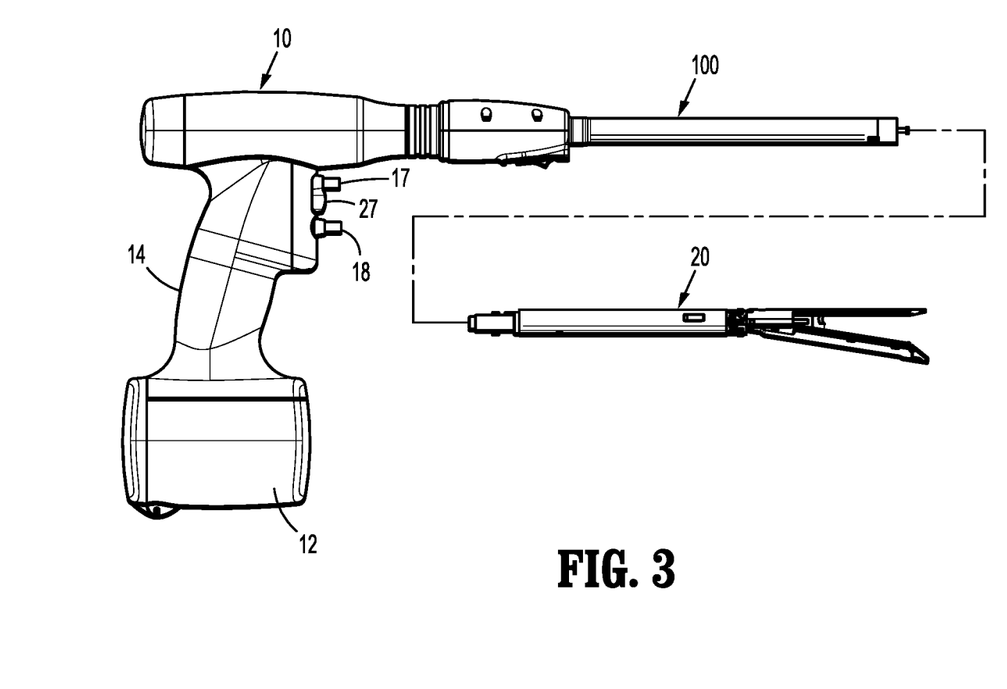
FIG. 3 is a perspective view of the intelligent surgical device of FIGS. 1 and 2, illustrating the adapter assembly connected thereto and illustrating the loading unit disconnected from the adapter assembly.
Figure 4:
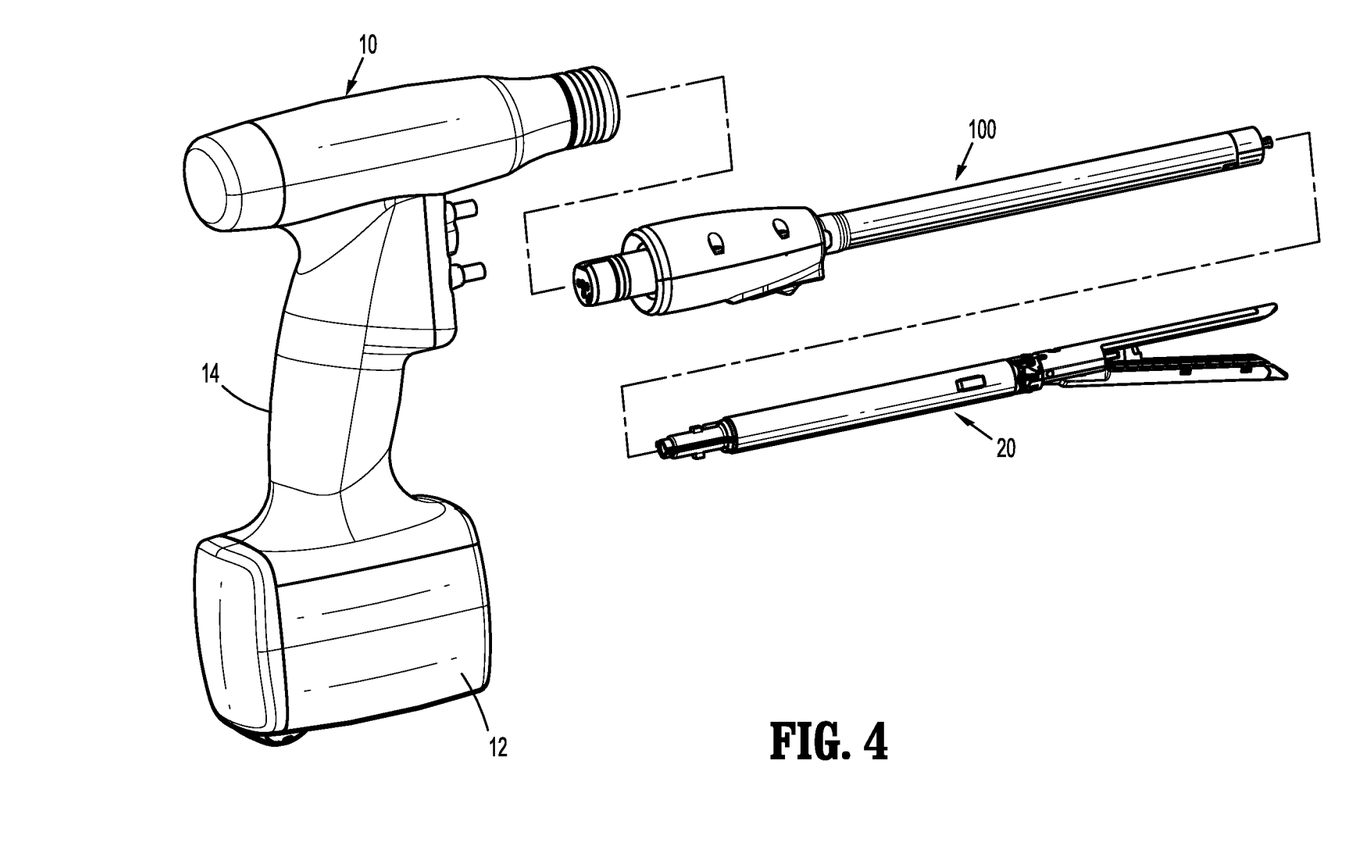
FIG. 4 is a perspective view of the intelligent surgical device of FIGS. 1-3, illustrating the adapter assembly disconnected therefrom and illustrating the loading unit disconnected from the adapter assembly.
Figure 5:
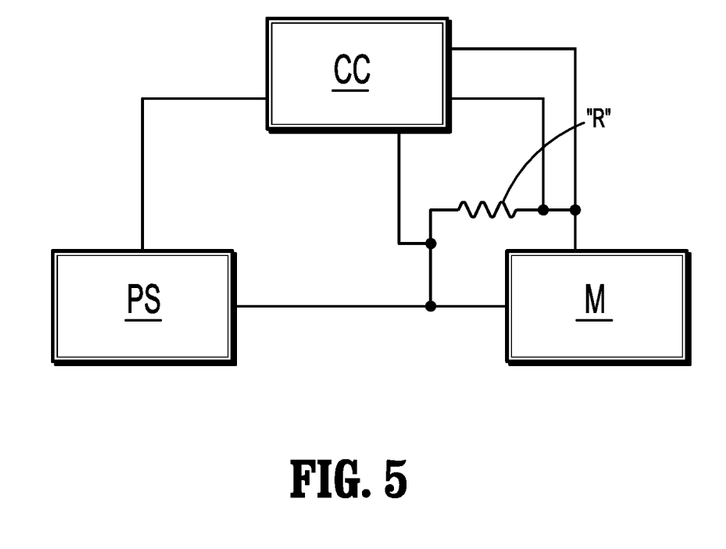
FIG. 5 is a schematic of a circuit diagram of a feedback system according to an embodiment of the present disclosure.

In accordance with the present disclosure, in order for intelligent surgical device 10 to identify the parameters of non-intelligent loading units 20, intelligent surgical device 10 includes, as seen in FIG. 5, a feedback system incorporated into or associated with the drive circuit or control circuit "CC" of the first drive motor "M" or second drive motor "M" of intelligent surgical device 10.

It is contemplated, in accordance with an embodiment of the present disclosure, the feedback system incorporates a highly toleranced resistor "R" with an extremely low resistance, about 0.05 ohms, that is added to a low side of an H-bridge responsible for driving the first drive motor or the second drive motor. In operation, the feedback system measures a voltage "V" across resistor "R." By measuring the voltage "V" drop across resistor "R," the feedback system may calculate an amount of current "I" flowing through resistor "R" using Ohm's Law:

$$V=IR$$

In a DC electric motor, such as first drive motor or second drive motor, current "I" is directly related to the amount of torque "T" being developed by using a relation, e.g., the Torque Constant (Km). Accordingly, the feedback system calculates the amount of torque "τ" being applied to first drive motor or second drive motor according to the following equation:

$$\tau=(Km)(I)$$

By factoring in the reductions in a transmission of surgical device 10 and of a screw drive of surgical device 10, the feedback system may determine an amount of linear force being applied to a firing rod in loading unit 20. Additionally, the feedback system needs to determine a linear position of the firing rod of loading unit 20 in order to ultimately determine if the torque being applied to first drive motor or second drive motor corresponds to a particular length of a staple cartridge loaded in loading unit 20. It is contemplated that an optical or magnetic encoder, a linear variable differential transformer (LVDT) or other method may be used to determine the linear position of the firing rod.

Figure 6:
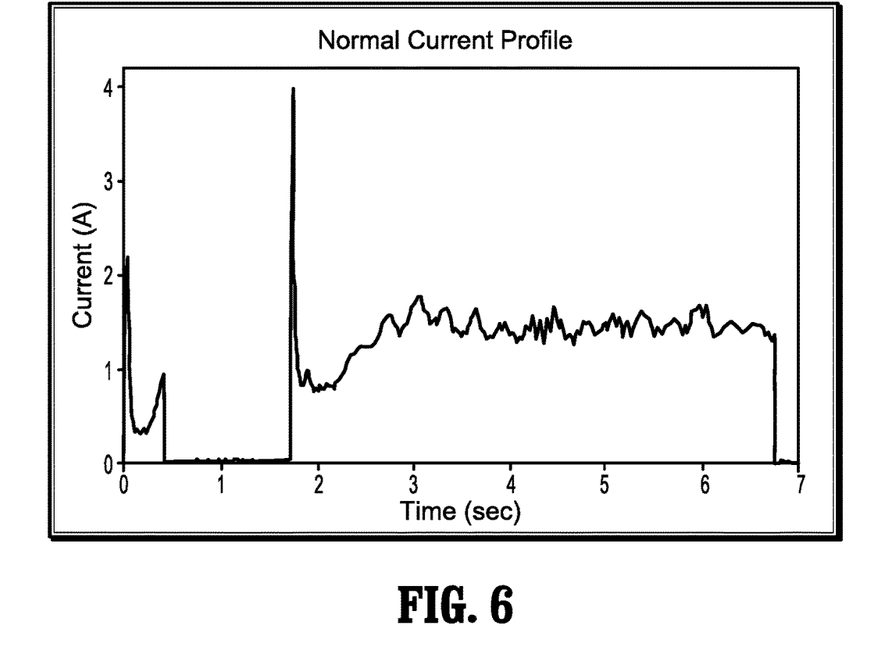
FIG. 6 is a chart illustrating a normal operating profile of current v. time for an intelligent surgical device operating an intelligent loading unit.

During a normal operating condition of surgical device 10, a certain or predetermined force profile is expected to be seen by the feedback system in the control circuitry of surgical device 10, e.g., either a current v. time profile (see FIG. 6) or a current v. distance profile (not shown). In operation, with the control circuitry monitoring current "I," when the firing rod of surgical device 10 is at a linear position corresponding with an end of a stroke for a particular staple cartridge length (i.e., 30 mm, 45 mm or 60 mm) and the feedback system of the control circuitry determines a higher than expected current "I" or current spike (as seen in FIG. 7), the control circuitry can reasonably assume that a firing sled of loading unit 20 has reached an end or a stop of the staple cartridge and/or loading unit 20.

Figure 7:
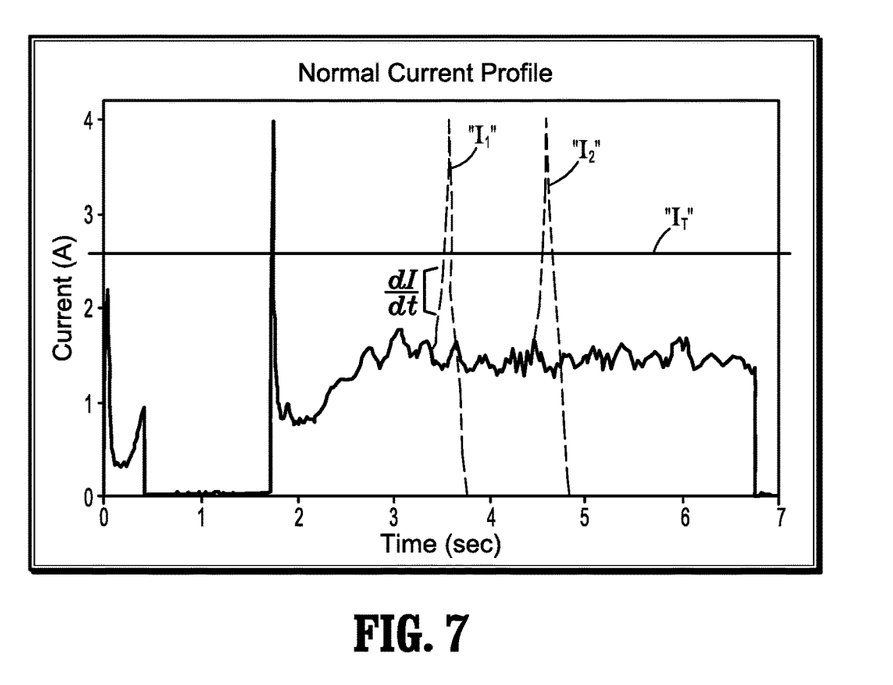
FIG. 7 is a chart illustrating an operating profile of current v. time for an intelligent surgical device operating a non-intelligent loading unit.

As seen in FIG. 7, a first current spike "$I_1$" is illustrated at a location when the firing sled of loading unit 20 has reached an end or a stop of the staple cartridge and/or loading unit 20 corresponding to approximately 30 mm. As also seen in FIG. 7, a second current spike "$I_2$" is illustrated at a location when the firing sled of loading unit 20 has reached an end or a stop of the staple cartridge and/or loading unit 20 corresponding to approximately 45 mm.

Each current spike "$I_1$" or "$I_2$" exceeds a predetermined threshold level "$I_T$" for current "I." The predetermined threshold level "$I_T$" for current "I" is selected so that if there is an increase in current "I" during the firing sequence, at a location prior to 30 mm for a 30 mm staple cartridge, prior to 45 mm for a 45 mm staple cartridge, or prior to 60 mm for a 60 mm staple cartridge, that surgical device 10 will continue to fire until the end or stop of the staple cartridge and/or loading unit 20 has been achieved, as described above. Premature increases in current "I," during the firing of surgical device 10, may be experienced if the path through the tissue through which loading unit 20 is acting on includes a segment of denser tissue, a change in the type of tissue, a prior deployed fastener or the like.

Additionally or alternatively, the control circuitry of surgical device 10 may also monitor a slope of current v. time (dI/dt) or current v. distance (dI/dx) to determine if an end of the staple cartridge has been reached. For example, if the feedback system determines that a rise in the slope has become excessively large, the control circuitry can also reasonably assume that a firing sled of loading unit 20 has reached an end or a stop of the staple cartridge and/or loading unit 20.

In accordance with the present disclosure, the control circuitry of surgical device 10 includes a loading unit lockout recognition system that functions and/or operates according to the same or similar principles to the feedback system described above. The loading unit lockout recognition system functions to determine whether a mechanical lockout of a staple cartridge loaded into loading unit 20 has been or has not been activated.

In use, the first time that a staple cartridge is loaded into loading unit 20 and the loading unit 20 is clamped by surgical device 10, surgical device 10 continues to drive forward slightly further than a clamped position for loading unit 20. If the loading unit lockout recognition system measures a sudden spike in current "I," corresponding to a rapid increase in torque "τ," the loading unit lockout recognition system of the control circuitry determines that a hard stop for the mechanical lockout of the staple cartridge in the loading unit 20 has been reached. Surgical device 10 may then relay the information to the user and the control circuitry will not allow surgical device 10 to be fired.

If the loading unit lockout recognition system does not measure a sudden spike in current "I," the loading unit lockout recognition system of the control circuitry concludes that the mechanical lockout of the staple cartridge in the loading unit 20 has not been activated. If the loading unit lockout recognition system concludes that the mechanical lockout of the staple cartridge in the loading unit 20 has not been activated, the control circuitry indicated to the surgical device 10 the presence of an un-fired staple cartridge and operation of surgical device 10 may continue as normal to fire loading unit 20.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical system for performing a surgical procedure, comprising:
    a surgical device including a drive motor and a feedback system coupled to the drive motor, the feedback system including a resistor and configured to calculate at least one of a voltage or a current across the resistor; and
    at least one loading unit configured for selective connection to the surgical device, the drive motor configured to actuate the at least one loading unit from a first condition to a second condition, the current or the voltage across the resistor changing as the at least one loading unit moves from the first condition towards the second condition, wherein the feedback system is further configured to change an amount of power delivered to the drive motor in response to detecting at least one of a voltage spike or a current spike across the resistor.

2. The surgical system according to claim 1, wherein the feedback system is configured to automatically change the amount of power delivered to the drive motor in response to detecting the at least one of the voltage spike or the current spike across the resistor.

3. The surgical system according to claim 1, wherein the surgical device further includes a control circuit in communication with the drive motor, the control circuit including the feedback system.

4. The surgical system according to claim 1, wherein the surgical device further includes a power source configured to provide the power to the drive motor.

5. The surgical system according to claim 4, wherein the surgical device further includes a handle housing, each of the power source, the drive motor, and the feedback system being disposed within the handle housing.

6. The surgical system according to claim 1, wherein the second condition of the loading unit is an end of a firing stroke.

7. The surgical system according to claim 6, wherein the current spike is associated with the end of the firing stroke of the loading unit.

8. A surgical system for performing a surgical procedure, the surgical system comprising:
a surgical device including a drive motor and a control circuit in communication with the drive motor; and
a loading unit configured for selective connection to the surgical device and actuatable by the drive motor from a first condition to a second condition, the control circuit being configured to detect when the loading unit is in the second condition based on a power provided to the drive motor, wherein the control circuit is configured to automatically change an amount of the power delivered to the drive motor in response to detecting at least one of a voltage spike or a current spike corresponding to an end of a firing stroke of the loading unit.

9. The surgical system according to claim 8, wherein the control circuit is further configured to monitor a voltage of the power being provided to the drive motor by a power source.

10. The surgical system according to claim 8, wherein the control circuit includes a resistor along which the power travels to the drive motor.

11. The surgical system according to claim 10, wherein the current spike detected by the control circuit is across the resistor.

12. An intelligent surgical device configured to selectively couple with and operate a non-intelligent loading unit, the non-intelligent loading unit having at least a first condition and a second condition, the intelligent surgical device comprising:
a power source;
a drive motor; and
a control circuit coupled to the drive motor, the control circuit including a resistor along which power being delivered to the drive motor by the power source travels, the control circuit configured to determine at least one of a voltage or a current across the resistor and to reduce or disable power delivered to the drive motor from the power source in response to the control circuit detecting at least one of a voltage spike or a current spike across the resistor.

13. The intelligent surgical device according to claim 12, further comprising a handle housing, wherein each of the power source, the drive motor, and the control circuit is disposed within the handle housing.

14. The intelligent surgical device according to claim 12, wherein the second condition of the non-intelligent loading unit is an end of a firing stroke.

15. The intelligent surgical device according to claim 14, wherein the current spike is associated with the end of the firing stroke of the non-intelligent loading unit.

* * * * *